United States Patent
Nikolic et al.

(10) Patent No.: US 9,907,893 B2
(45) Date of Patent: Mar. 6, 2018

(54) SYSTEM OF MEDICAL TREATMENT UNITS AND PERIPHERAL DEVICES

(75) Inventors: Dejan Nikolic, Frankfurt am Main (DE); Christoph Koenig, Wiesbaden/Auringen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 12/096,832

(22) PCT Filed: Dec. 1, 2006

(86) PCT No.: PCT/EP2006/011571
§ 371 (c)(1),
(2), (4) Date: Jun. 10, 2008

(87) PCT Pub. No.: WO2007/065609
PCT Pub. Date: Jun. 14, 2007

(65) Prior Publication Data
US 2008/0312960 A1 Dec. 18, 2008

(30) Foreign Application Priority Data
Dec. 10, 2005 (DE) .................. 10 2005 059 131

(51) Int. Cl.
*G06Q 50/22* (2012.01)
*G06Q 50/24* (2012.01)
(Continued)

(52) U.S. Cl.
CPC .............. *A61M 1/16* (2013.01); *A61M 1/14* (2013.01); *A61M 1/34* (2013.01); *A61M 1/36* (2013.01);
(Continued)

(58) Field of Classification Search
CPC ........ G06Q 50/22; G06Q 10/06; G06Q 10/10; G06Q 50/24
(Continued)

(56) References Cited

U.S. PATENT DOCUMENTS 6,332,094 B1 12/2001 Gorman
2002/0183585 A1* 12/2002 Willems et al. ............... 600/17
(Continued)

FOREIGN PATENT DOCUMENTS

| DE | 102004011264 | 9/2004 |
| WO | WO 02/078775 A2 | 10/2002 |
| WO | WO 04/056263 | 7/2004 |

OTHER PUBLICATIONS

PCT/EP2006/011571 International Search Report, dated Aug. 6, 2007.

*Primary Examiner* — Maroun Kanaan
(74) *Attorney, Agent, or Firm* — Kilyk & Bowersox, P.L.L.C.

(57) ABSTRACT

The invention relates to a system of a plurality of medical treatment units that are respectively associated with a patient, and a plurality of peripheral appliances also respectively associated with a patient. The peripheral appliances transmit control signals and patient signals to the treatment units, while the treatment units receive the control signals and patient signals from the peripheral appliances. The present invention ensures that the treatment units do not receive patient signals from other peripheral appliances that are not associated with the particular patient. The operating staff allocate a peripheral appliance to a patient and confirm the successful association of the peripheral appliance with the treatment unit allocated to the patient.

10 Claims, 2 Drawing Sheets

(51) Int. Cl.
*A61M 1/16* (2006.01)
*A61M 1/14* (2006.01)
*A61M 1/34* (2006.01)
*A61M 1/36* (2006.01)

(52) U.S. Cl.
CPC ......... *G06Q 50/22* (2013.01); *A61M 2205/33* (2013.01); *A61M 2205/35* (2013.01); *A61M 2205/3561* (2013.01); *A61M 2205/52* (2013.01)

(58) Field of Classification Search
USPC .......................................................... 705/2, 3
See application file for complete search history.

(56) References Cited

U.S. PATENT DOCUMENTS

| 2004/0019464 | A1* | 1/2004 | Martucci et al. ............. 702/189 |
| 2004/0220832 | A1 | 11/2004 | Moll et al. |
| 2006/0089539 | A1* | 4/2006 | Miodownik et al. ......... 600/300 |
| 2006/0136998 | A1* | 6/2006 | Oowaki et al. .................... 726/5 |
| 2009/0184842 | A1* | 7/2009 | Baldus et al. ........... 340/870.07 |

\* cited by examiner

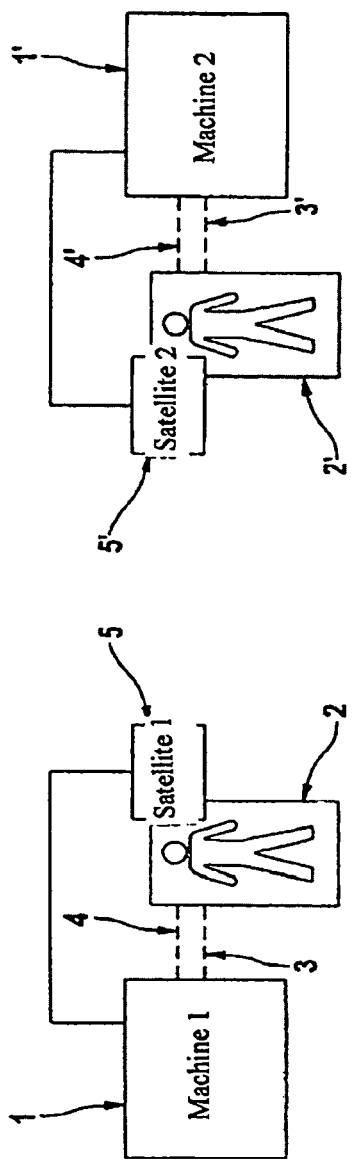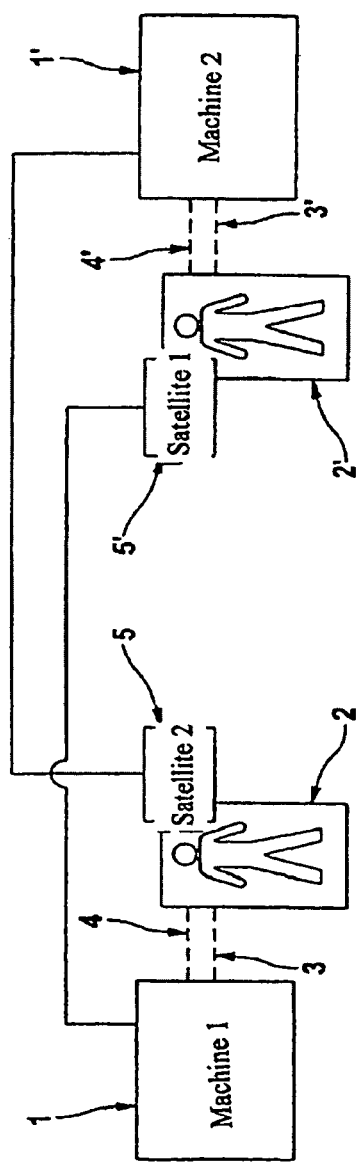

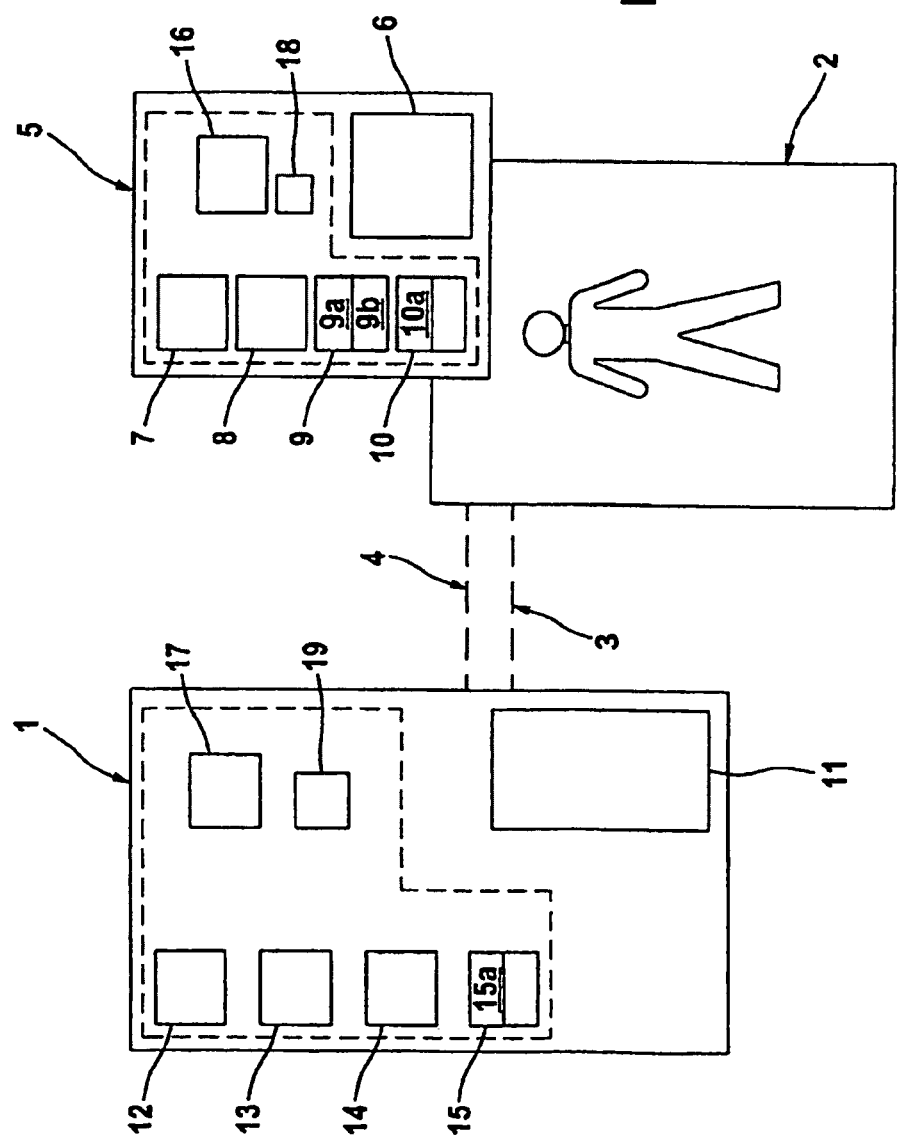

SYSTEM OF MEDICAL TREATMENT UNITS AND PERIPHERAL DEVICES

FIELD OF THE INVENTION

The present invention relates to a system comprising a plurality of medical treatment units and a plurality of peripheral devices, where each treatment unit and each peripheral device are assigned to a particular patient.

BACKGROUND OF THE INVENTION

Various treatment units, to which patients are connected or which are connected to patients, are used for the treatment of patients in medical technology. The connection between the patient and a treatment unit generally takes place via tubes or lines. A known treatment unit includes, for example, dialysis machines with an extracorporeal blood circuit.

Additionally, it is known to operate medical treatment units together with one or more peripheral devices. Such peripheral devices serve, for example, to monitor the patient during the treatment, with the collected data being transmitted to the treatment unit.

Although there is a fixed connection between the treatment unit and the patient via tubes or lines, the data transfer between the peripheral device and the treatment unit can take place wirelessly, for example by radio or light signals. The operator can thus immediately detect the allocation between the treatment unit and the patient on the basis of the fixed connection, but cannot immediately detect the allocation between the peripheral device and the treatment unit.

If a plurality of treatment units and peripheral devices are operated together in a single treatment area, it is necessary in each case to allocate a treatment unit and a peripheral device to a patient and to create a connection from the respective peripheral device to the respective treatment unit for the data transfer. An incorrect allocation of a peripheral device and a treatment unit would result in the data of one patient being transferred to the treatment unit of another patient.

Since, in the extreme case, such a mismatched data transfer can lead to life-threatening complications during treatment, it must be ensured that the correct allocation is made between the peripheral device and the patient on the one hand, and between the peripheral device and the treatment unit on the other hand. This is especially problematic with the known peripheral devices and treatment units, since the allocation between peripheral device and treatment unit cannot easily be detected by personnel in the case of a wireless connection.

If a plurality of devices that are communicating with one another are operated at the same time, use is generally made of so-called identification (ID) signals, which can detect which peripheral device signal is being received. U.S. Pat. No. 6,332,094 B1, for example, describes a pulsometer, which transfers the pulse signals together with an identification signal wirelessly to a receiver.

SUMMARY OF THE INVENTION

One aspect of the present invention is to increase the reliability and flexibility during the operation of a plurality of medical treatment units and peripheral devices in a common treatment area.

In the system according to the present invention, which comprises a plurality of medical treatment units and peripheral devices, wherein each treatment unit and each peripheral device are allocated to one patient, both the allocation of the peripheral device to the patient and the allocation of the peripheral device to the treatment unit are monitored. For this purpose, the peripheral devices comprise means for monitoring the allocation of a peripheral device to a patient, and the treatment units comprise means for monitoring the allocation of a peripheral device to the treatment unit. Additionally, the peripheral devices comprise means for logging on the peripheral device with a treatment unit, and the treatment units comprise means for inputting an acknowledgement of a successful allocation of a peripheral device to the treatment unit.

A check is first made to establish whether a peripheral device is allocated to a patient. If a peripheral device is allocated to a patient, the peripheral device then sends a log-on signal to the treatment unit that is allocated to the patient. The system according to the present invention requires an acknowledgement of the successful allocation of the peripheral device to the treatment unit. Only when the allocation has been acknowledged can the data transfer between the peripheral device and the treatment unit take place.

For the logging-on of the peripheral devices with the treatment units, the peripheral devices according to the invention comprise means for sending control signals to the treatment units, and the treatment units comprise means for receiving control signals from the peripheral devices. For the data transfer, the peripheral devices comprise means for sending patient signals to the treatment units, and the treatment units comprise means for receiving patient signals from the peripheral devices. The data transfer between the peripheral device and the treatment unit can in principle not only take place uni-directionally, but also bi-directionally.

When a successful allocation of a peripheral device to a patient has taken place, the system according to the present invention requires the operator to check the allocation of the peripheral device to the treatment unit that is allocated to the patient. This eliminates the possibility of an incorrect data transfer taking place.

In a preferred embodiment, the means for monitoring the allocation of a peripheral device to a treatment unit comprise a timing element with a preset timing constant, which is started after reception of the log-on signal. The data transfer from the peripheral device to the treatment unit is released only when the operator has acknowledged the correct allocation of peripheral device and treatment unit within the preset timing constant, which for example can be between 1 and 60 seconds, or between one and several minutes. The operator is thus required to immediately check the logging-on of the peripheral device with the treatment unit, so that there is no risk of the operator being distracted by other tasks.

In another preferred embodiment, the means for monitoring the allocation of a peripheral device to a treatment unit are designed such that the data transfer from the peripheral device to the treatment unit is not released when log-on signals from a plurality of peripheral devices have been received by one treatment unit within the timing constant. This ensures that only one peripheral device can be allocated to each treatment unit.

In another preferred embodiment, the allocation of a peripheral device to a treatment unit takes place using identification signals. In a first alternative embodiment, the corresponding identification signals of the individual peripheral devices are stored in a non-volatile manner in the peripheral devices, and the reference signals allocated to the identification signals of the peripheral devices for recognition of the respective peripheral devices are stored in a non-volatile manner in the treatment units. The peripheral devices and treatment units have suitable memories for this purpose. In another, especially preferred embodiment, the identification signal of the peripheral device is sent to the treatment unit together with the log-on signal after successful allocation of peripheral device to the patient, and the treatment unit sends its own identification signal to the logged-on peripheral device after acknowledgement of the successful logging-on by the operator. Both identification signals are then used during the data transfer.

Additionally, the means for monitoring the allocation of a peripheral device to the patient can comprise means for manual input. When the operator has allocated the peripheral device to the patient, e.g. has fitted the peripheral device to the patient, the operator acknowledges the successful allocation by a manual input. The allocation between peripheral device and patient has thus taken place.

In an alternative embodiment, the allocation of the peripheral device to the patient can take place automatically. For this purpose, the means for monitoring the allocation preferably comprise means for the automatic recognition of a peripheral device allocated to the patient, for example a proximity sensor or the like. A successful allocation between peripheral device and patient can also be determined by the success of, for example, a functional test of the peripheral device.

The problem of an incorrect allocation occurs not only with a non-unequivocal allocation of peripheral device and treatment unit, but also with a non-unequivocal treatment unit allocation. The data transfer is therefore prevented when, for example, two treatment units try to connect to a peripheral device.

The system of the present invention creates a high degree of flexibility with the device allocation, since the individual peripheral devices can be exchanged with one another and allocated to the individual treatment units without the risk of an incorrect data transfer.

BRIEF DESCRIPTION OF THE DRAWINGS

An example of embodiment of the invention is explained below in greater detail by reference to the drawings.

FIG. 1 shows a schematic representation of a correct allocation between two peripheral devices and two treatment units, FIG. 2 shows the arrangement of FIG. 1, wherein the peripheral devices are allocated to the incorrect treatment units, and FIG. 3 shows the main components of a treatment unit and a peripheral device.

DETAILED DESCRIPTION OF THE DRAWINGS

FIG. 1 shows two medical treatment units (machines) 1, 1', for example extracorporeal blood treatment apparatuses with an extracorporeal blood circuit. A patient 2, 2' is connected to each treatment unit 1, 1'. In the case of an extracorporeal blood treatment, patient 2, 2' is connected to blood treatment apparatus 1, 1' via a venous and arterial tube line 3, 4; 3', 4'. A fixed allocation between the patient and the treatment unit is thus made. Moreover, a peripheral device (satellite) 5, 5', for example a blood pressure monitor, is allocated in each case to the two patients 2, 2'.

Peripheral devices 5, 5' monitor the patient's bodily functions, for example the blood pressure, and transfer the data to the respective treatment unit to which the patient is connected.

FIG. 1 shows the correct allocation of a first peripheral device and a first patient, and a second peripheral device and second patient on the one hand, and the first peripheral device and first treatment unit, and the second peripheral device and second treatment unit on the other hand. However, FIG. 2 shows an incorrect allocation between the peripheral devices and treatment units. In the case of the incorrect allocation shown in FIG. 2, first treatment unit 1 receives the data of second peripheral device 5', whilst second treatment unit 1' receives the data of first peripheral device 5.

The communication between peripheral devices 5, 5' and treatment units 1, 1' comprises both control signals, which are used for the logging-on (log-on signal) and identification (identification signal ID) of the devices, as well as patient signals, which are used for the actual data transfer, for example of the measured blood pressure from the blood pressure monitor to the extracorporeal blood treatment apparatus.

The system according to the present invention comprises at least two medical treatment units and two peripheral devices. The individual components of a treatment unit and a peripheral device as well as the individual steps for the allocation of patient, peripheral device and treatment unit are described below by reference to FIG. 3.

Peripheral device 5, for example a blood pressure monitor, comprises various components 6, shown only schematically, for monitoring the patient, for example the components for monitoring the blood pressure. For the communication with respective treatment unit 1, peripheral device 5 comprises means 7 for sending control signals to the treatment unit and means 8 for sending patient signals to the treatment unit. The data transfer preferably takes place bi-directionally, the data transfer means comprising both means for sending and for receiving control signals and patient signals. Furthermore, peripheral device 5 comprises means 9 for monitoring the allocation of the peripheral device to patient 2 and means 10 for logging on the peripheral device with respective treatment unit 1.

Treatment unit 1, for example a blood treatment apparatus with an extracorporeal blood circuit, comprises various components 11, represented only schematically, for the treatment of patient 2, for example a dialyser, pumps etc. Patient 2 is fixedly connected to treatment unit 1, for example via a venous and arterial blood line 3, 4. A fixed allocation between patient and treatment unit is thus provided.

For the communication with respective peripheral device 5, treatment unit 1 comprises, in the case of a bi-directional data transfer, means 12 for sending and receiving control signals to and from the peripheral device and means 13 for sending and receiving patient signals to and from the peripheral device. Furthermore, the treatment unit comprises means 14 for inputting an acknowledgement of a successful allocation of the peripheral device to the treatment unit and means 15 for monitoring the allocation of the peripheral device to the treatment unit.

The data transfer between treatment unit 1 and peripheral device 5 takes place by radio, the transmitter and receiver and interfaces required for this generally being known to a person of ordinary skill in the art. The peripheral device and the treatment unit preferably permit a bi-directional data transfer, but it is also possible for the transfer of data, which comprise both control signals as well as patient signals, to take place solely from the peripheral device to the treatment unit.

The function of the treatment units and peripheral devices is described in detail below.

The operator first selects a peripheral device 5, for example a blood pressure monitor, from available peripheral devices 5, 5'. The operator then allocates the selected peripheral device 5 to a specific patient 2. The allocation can take place by the peripheral device being connected to the patient. This procedure is monitored by means 9 for monitoring the allocation of the peripheral device to the patient. For this purpose, means 9 for monitoring the allocation comprise means 9a for a manual input, for example a switch or push-button. The switch or push-button is actuated by the operator when the peripheral device is connected to the patient.

Instead of means 9a for the manual input, means 9b can be provided for the automatic recognition of the peripheral device allocated to the patient. It is however also possible to provide both means for manual input 9a as well as means for automatic recognition 9b. The automatic recognition of the allocation can take place for example via a proximity sensor, which detects the allocation to the patient when the peripheral device is fitted. It is however also possible to recognize the allocation to the patient automatically by the fact that a test routine has been successfully completed, which is only carried out when the peripheral device is connected to the patient.

After the successful allocation of peripheral device 5 to patient 2, peripheral device 5 sends a log-on signal to respective treatment unit 1. Means 9a, 9b for the manual input or automatic recognition are then deactivated, so that the possibility of incorrect inputs is eliminated.

Means 15 for monitoring the allocation of the peripheral device to the treatment unit comprise a timing element 15A with a preset timing constant, for example 30 to 60 seconds, which is started with the registration of the log-on signal. If, within this time window, logging-on attempts by other peripheral devices take place, the routine is interrupted so that renewed logging-on and acknowledgement is required. It is however also possible for treatment unit 1 no longer to accept the logging-on attempt of another peripheral device 5' within this time window.

The successful allocation of peripheral device and treatment unit is displayed to the operator. For this purpose, peripheral device 5 and/or the treatment unit comprises an optical and/or acoustic display unit 16, 17. The operator must check within the time window of 60 seconds whether the allocation is correct. If this is the case, the operator acknowledges the allocation by actuating means 14 for the input of the acknowledgement at the treatment unit, for example by actuating a switch or push-button. If, on the other hand, a manual acknowledgement of the correct allocation by the operator does not take place within this time window, the procedure is interrupted, so that renewed logging-on is required.

Although there is only a wireless connection between peripheral device 5 and treatment unit 1 which does not require a connection of the peripheral device to the treatment unit, the operator can actively recreate the allocation of the peripheral device and treatment unit by acknowledging the successful allocation at the treatment unit which has been allocated to the peripheral device. The manual acknowledgement of the allocation corresponds to inserting a plug into a socket, which is otherwise required with a conventional connection of the device using a connection cable.

Only when the allocation has been successful and has been acknowledged is the transfer of the patient signals, for example the measured values for the patient's blood pressure, started, whereby means 13 for receiving patient signals from allocated peripheral device 5 are activated for the actual data transfer.

In order to identify the patient signals, peripheral device 5 and treatment unit 1 each comprise a memory 18, 19, an identification signal ID being stored in a non-volatile manner in memory 18 of the peripheral device and a reference signal allocated to the respective peripheral device being stored in a non-volatile manner in memory 19 of the treatment unit.

In the course of the logging-on of the peripheral device with the treatment unit, the peripheral device sends, together with the log-on signal, identification signal ID which is stored in memory 18 of the peripheral device. The treatment unit then compares the reference signals stored in memory 19 with received identification signal ID of the peripheral device. If identification signal ID and reference signal agree, the treatment unit has recognized the appropriate peripheral device. This eliminates the possibility of the treatment unit receiving the patient signals of other peripheral devices.

Apart from the static allocation, in which identification and reference signals are stored respectively in memories 18, 19 of peripheral device 5 and treatment unit 1, which create a fixed allocation between peripheral device and treatment unit, a dynamic allocation is also possible.

In the case of the dynamic allocation, identification signal ID stored in a non-volatile manner in memory 18 of peripheral device 5 is sent during logging-on together with the log-on signal to the treatment unit, which the treatment unit stores in memory 19. After acknowledgement of the successful allocation of peripheral device and treatment unit, the treatment unit sends an identification signal ID of the treatment unit stored in memory 19 to the peripheral device. During the following data transfer, both identification signals are then used, an incorrect allocation of peripheral device and treatment unit being prevented by the operator acknowledging the logging-on of the peripheral device with the treatment unit.

The invention claimed is:

1. A system for matching multiple peripheral devices and medical treatment units with the correct patients comprising:
a plurality of peripheral devices and a plurality of medical treatment units comprising: a first medical treatment unit and a first peripheral device being allocated to a first patient, and a second medical treatment unit and a second peripheral device being allocated to a second patient, wherein the first medical treatment unit is a first blood treatment apparatus comprising a first dialysis machine having a first extracorporeal blood circuit, and the second medical treatment unit is a second blood treatment apparatus comprising a second dialysis machine having a second extracorporeal blood circuit,
wherein the first peripheral device comprises a first blood pressure monitor that is configured to monitor the first patient's blood pressure and is wirelessly connected to the first dialysis machine of the first medical treatment unit, and the second peripheral device comprises a second blood pressure monitor that is configured to monitor the second patient's blood pressure and is wirelessly connected to the second dialysis machine of the second medical treatment unit,
each peripheral device comprising:
a patient monitor having components configured to monitor a patient and configured to measure blood pressure of the patient;

a control signal sending device configured to send control signals to the dialysis machine of the respective medical treatment unit, a patient signal sending device configured to send patient signals comprising data relating to the patient's blood pressure to the dialysis machine of the respective medical treatment unit, a first monitoring device configured to monitor an allocation, of the respective first or second blood pressure monitor, to the patient, a memory storage device for non-volatile storage of an identification signal corresponding to the blood pressure monitor of the peripheral device, and a log-on device configured to send a log-on signal and the identification signal from the blood pressure monitor of the peripheral device to the respective dialysis machine of the respective medical treatment unit, said log-on device cooperating with the control signal sending device and the first monitoring device; and each medical treatment unit comprising:

a control signal receiving device configured to receive control signals from the control signal sending device of the respective peripheral device, a patient signal receiving device configured to receive patient signals from the patient signal sending device of the respective peripheral device, a memory storage device for non-volatile storage of a reference signal corresponding to the dialysis machine of the medical treatment unit allocated to the blood pressure monitor of the respective peripheral device, an acknowledgement device configured to allow an operator to input the acknowledgement of an allocation of the respective blood pressure monitor of the respective peripheral device to the dialysis machine of the respective medical treatment unit, wherein the acknowledgement device comprises a switch or push-button configured to allow the operator to input the acknowledgement, and a second monitoring device configured to monitor the allocation of the blood pressure monitor of the respective peripheral device to the dialysis machine of the respective medical treatment unit, said second monitoring device cooperating with the control signal receiving device, the patient signal receiving device, and the acknowledgement device, wherein the second monitoring device comprises a timing element with a preset timing constant configured to be started after the log-on signal has been received, and a check is made to establish whether the allocation of a blood pressure monitor of a peripheral device to a dialysis machine of a treatment unit has been acknowledged within the preset timing constant, and wherein the second monitoring device further comprises a comparison device configured to compare the identification signal of the blood pressure monitor of the peripheral device with the reference signal of the dialysis machine of the treatment unit allocated to the blood pressure monitor of the peripheral device, said comparison device cooperable with the patient signal receiving device and configured to activate the patient signal receiving device when the identification signal and the reference signal match, wherein when the allocation of the first blood pressure monitor of the first peripheral device to the first dialysis machine of the first medical treatment unit has been acknowledged and the identification signal of the first blood pressure monitor of the first peripheral device and the reference signal of the first dialysis machine of the first medical treatment unit are determined to match by the comparison device, the patient signal receiving device of the first medical treatment unit is configured to be activated, and wherein when the allocation of the second blood pressure monitor of the second peripheral device to the second dialysis machine of the second medical treatment unit has been acknowledged and the identification signal of the second blood pressure monitor of the second peripheral device and the reference signal of the second dialysis machine of the second medical treatment unit are determined to match by the comparison device, the patient signal receiving device of the second medical treatment unit is configured to be activated, wherein the patient signal receiving device of the first medical treatment unit is configured such that it is not activated if the log-on signals are received from more than one peripheral device within the preset timing constant, and wherein when the first blood pressure monitor of the first peripheral device is allocated to the second dialysis machine of the second medical treatment unit, the patient signal receiving device of the second medical treatment unit is configured to prevent activation, and wherein when the second blood pressure monitor of the second peripheral device is allocated to the first dialysis machine of the first medical treatment unit, the patient signal receiving device of the first medical treatment unit is configured to prevent activation.

2. The system of claim 1, wherein, for each peripheral device, the respective log-on device cooperates with the respective control signal sending device and is configured to send an identification signal of the respective peripheral device together with the respective log-on signal to the respective treatment unit.

3. The system of claim 1, wherein the first monitoring device comprises a device configured to receive a manual input.

4. The system of claim 1, wherein the first monitoring device comprises a device configured to automatically recognize when a peripheral device is allocated to the patient.

5. The system of claim 1, wherein the first monitoring device or the acknowledgement device comprises a display device configured to display the allocation of a peripheral device and a treatment unit.

6. The system of claim 1, wherein the control signal sending device, the patient signal sending device, the control signal receiving device, and the patient signal receiving device are configured for wireless transmission of signals.

7. A system for allocating a peripheral device, that measures a bodily function of a patient, to a blood treatment apparatus for medically treating the patient, said blood treatment apparatus comprising a dialysis machine having an extracorporeal blood circuit, wherein the system comprises:

a first allocation monitoring device configured to monitor a state of allocation of the peripheral device to the patient; and a second allocation monitoring device configured to monitor the allocation of the peripheral device to the blood treatment apparatus using an acknowledgment routine, said acknowledgement routine starting when a first log-on signal is registered by said second allocation monitoring device, wherein the peripheral device comprises:
- a patient monitor comprising a blood pressure monitor having components configured to monitor the patient and configured to measure at least blood pressure of the patient;
- a patient signal sending device configured to wirelessly send patient signals comprising data relating to at least the patient's blood pressure to the dialysis machine of the blood treatment apparatus;
- a memory storage device for non-volatile storage of an identification signal corresponding to the blood pressure monitor of the peripheral device, and
- a log-on device configured to wirelessly send the first log-on signal from the blood pressure monitor of the peripheral device to the dialysis machine of the blood treatment apparatus when said first allocation monitoring device determines that the blood pressure monitor of the peripheral device is allocated to the patient;

the blood treatment apparatus comprising:
- a memory storage device for non-volatile storage of a reference signal corresponding to the dialysis machine of the blood treatment apparatus allocated to the blood pressure monitor of the peripheral device,
- an acknowledgement device configured to allow an operator to input an acknowledgement that the blood pressure monitor of the peripheral device is to be allocated to the dialysis machine of the blood treatment apparatus,
  - wherein the acknowledgement device comprises a switch or push-button configured to allow the operator to input the acknowledgement, and
- a patient signal receiving device configured to begin receiving patient signals from the blood pressure monitor of the peripheral device following input of the acknowledgment by the operator, wherein the second allocation monitoring device comprises a timing element that is started with a registration of said first log-on signal, wherein the timing element of the second allocation monitoring device is configured with a preset timing constant, wherein the second allocation monitoring device further comprises a comparison device configured to compare the identification signal of the blood pressure monitor of the peripheral device with the reference signal of the dialysis machine of the blood treatment apparatus allocated to the blood pressure monitor of the peripheral device, said comparison device cooperable with the patient signal receiving device and configured to activate the patient signal receiving device when the identification signal and the reference signal match, wherein, if an acknowledgement from the acknowledgement device is received within an amount of time from the time of the registration of said first log-on signal, and the amount of time is less than said preset timing constant, and if the identification signal of the blood pressure monitor of the peripheral device and the reference signal of the dialysis machine of the blood treatment apparatus are determined to match by the comparison device, the patient signal receiving device begins receiving patient signals from the blood pressure monitor of the peripheral device, and wherein said acknowledgement routine is interrupted such that renewed logging-on is required prior to the beginning of a subsequent acknowledgment routine if the amount of time from the time of the registration of said first log-on signal is greater than said preset timing constant and an acknowledgement from the acknowledgement device has not been received, or if a second log-on signal is received from a second peripheral device within an amount of time from the time of the registration of said first log-on signal, which is less than said preset timing constant.

8. The system of claim 7, wherein the first monitoring device comprises a device configured to receive a manual input.

9. The system of claim 8, wherein the device configured to receive a manual input is a button.

10. The system of claim 7, wherein the peripheral device and/or the blood treatment unit comprises a optical and/or acoustic display unit configured to display the allocation of a peripheral device.

* * * * *